(12) United States Patent
Padmanabhan et al.

(10) Patent No.: US 10,246,529 B2
(45) Date of Patent: Apr. 2, 2019

(54) PROCATALYST FOR POLYMERIZATION OF OLEFINS

(71) Applicant: SABIC GLOBAL TECHNOLOGIES B.V., Bergen Op Zoom (NL)

(72) Inventors: Sudhakar R. Padmanabhan, Riyadh (SA); Khalid Abdullah Al-Bahily, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/541,088

(22) PCT Filed: Jan. 20, 2016

(86) PCT No.: PCT/EP2016/051052
§ 371 (c)(1),
(2) Date: Jun. 30, 2017

(87) PCT Pub. No.: WO2016/116469
PCT Pub. Date: Jul. 28, 2016

(65) Prior Publication Data
US 2018/0002462 A1 Jan. 4, 2018

Related U.S. Application Data

(60) Provisional application No. 62/158,580, filed on May 8, 2015.

(30) Foreign Application Priority Data

Jan. 21, 2015 (EP) .................................. 15151903

(51) Int. Cl.
*C08F 10/06* (2006.01)
*C07F 7/28* (2006.01)

(52) U.S. Cl.
CPC ............... *C08F 10/06* (2013.01); *C07F 7/28* (2013.01)

(58) Field of Classification Search
None
See application file for complete search history.

(56) References Cited

U.S. PATENT DOCUMENTS 4,384,087 A   5/1983  Capshew
4,414,132 A   11/1983 Goodall et al.
(Continued)

FOREIGN PATENT DOCUMENTS

EP   0501741 A1   9/1992
EP   1222214 B1   7/2002
(Continued)

OTHER PUBLICATIONS

"Perodic System of the Elements," Handbook of Chemistry and Physics, CRC Press; 1989-1990, 70th Edition.
(Continued)

*Primary Examiner* — Catherine S Branch
(74) *Attorney, Agent, or Firm* — Cantor Colburn LLP (57) ABSTRACT

The invention relates to a procatalyst for polymerization of olefins. The invention also relates to a process for preparing said procatalyst. Furthermore, the invention is directed to a catalyst system for polymerization of olefins comprising the said procatalyst, a co-catalyst and optionally an external electron donor; a process of preparing polyolefins by contacting an olefin with said catalyst system and to polyolefins obtained or obtainable by said process. The invention also relates to the use of said procatalyst in the polymerization of olefins.

17 Claims, 5 Drawing Sheets

(56) References Cited

U.S. PATENT DOCUMENTS

| | | | |
|---|---|---|---|
| 4,978,648 | A | 12/1990 | Barbe et al. |
| 5,077,357 | A | 12/1991 | Job |
| 5,106,806 | A | 4/1992 | Job |
| 5,556,820 | A | 9/1996 | Funabashi et al. |
| 2010/0130710 | A1 | 5/2010 | Chen |
| 2010/0174038 | A1 | 7/2010 | Hirahata et al. |

FOREIGN PATENT DOCUMENTS

| | | | | |
|---|---|---|---|---|
| EP | 1538167 | A1 | 6/2005 | |
| EP | 1783145 | A1 | 5/2007 | |
| EP | 2027164 | B1 | 8/2012 | |
| WO | 9632427 | A1 | 10/1996 | |
| WO | 0123441 | A1 | 4/2001 | |
| WO | WO-2013124063 | A1 * | 8/2013 | ............ C08F 10/00 |
| WO | 2015091984 | A1 | 6/2015 | |

OTHER PUBLICATIONS

International Search Report; International Application No. PCT/EP2016/051052; International Filing Date: Jan. 20, 2016; dated Apr. 18, 2016; 4 pages.

Pasquini, N (ed.) "Polypropylene handbook," Carl Hanser Verlag Munich; 2005, 11 Pages, 2nd edition, Chapter 6.2.

Written Opinon; International Application No. PCT/EP2016/051052; International Filing Date: Jan. 20, 2016; dated Apr. 18, 2016; 5 pages.

* cited by examiner

PROCATALYST FOR POLYMERIZATION OF OLEFINS

This application is a national stage application of PCT/EP2016/051052, filed Jan. 20, 2016, which claims priority to European Patent Application Number 15151903.0 filed Jan. 21, 2015, and U.S. Provisional Application 62/158,580 filed May 8, 2015, all of which are hereby incorporated by reference in their entirety.

BACKGROUND

The invention relates to a procatalyst for polymerization of olefins, a process for preparing said procatalyst, a catalyst system for polymerization of olefins comprising the said procatalyst, a co-catalyst and optionally an external electron donor; a process of preparing polyolefins by contacting an olefin with said catalyst system and to polyolefins obtainable by said process. The invention also relates to the use of said procatalyst in the polymerization of olefins.

Catalyst systems and their components that are suitable for preparing a polyolefin are generally known. One type of such catalysts is generally referred to as Ziegler-Natta catalysts. The term "Ziegler-Natta" is known in the art and it typically refers to catalyst systems comprising a transition metal-containing solid catalyst compound (also typically referred to as a procatalyst); an organometallic compound (also typically referred to as a co-catalyst) and optionally one or more electron donor compounds (e.g. external electron donors). Document EP2027164B1 discloses a process for preparing a polymerization catalyst component.

SUMMARY

The present teachings are related to a procatalyst having a magnesium support that is prepared using a simple manner. In an aspect, a combination of an alkyl magnesium and a Grignard is used. The method of EP2027164B1 uses only a Grignard for the magnesium support. In an aspect, an additional step is present in which the solid support is precipitated with the use of a tetrahalogensilane, preferably tetrachlorosilane.

According to the present teachings, the ratio between the alkyl magnesium and the Grignard reagent can be tuned; with increasing amounts of alkyl magnesium, the chloride content is increased which in turn leads to decreased ethoxide content. By adjusting the amount of tetrahalogensilane the ethoxide content may be adjusted; the higher the amount of tetrahalogensilane, the lower the ethoxide content of the support; this reflects directly in the catalyst allowing more control of the polymerization. Moreover, the titanium content based can be adjusted by adjusting the ethoxide content which is turn can be adjusted according to the level of silyl chloride that is added. When the amount of ethoxide is less, the amount of anchored titanium is also less and the polymer produces has a higher isotacticity.

The process according to the present invention allows to obtain catalyst composition providing polymers having a higher isotacticity and lower xylene solubles.

Aspects of the Invention

A first aspect, relates to a process for preparing a procatalyst suitable for preparing a catalyst composition for olefin polymerization, said process comprising the steps of:
i) contacting a compound $R^4_z MgX^4_{2-z}$ and a compound $MgR^{4'}_2$ with an alkoxy- or aryloxy-containing silane compound to give a first intermediate reaction product, being a solid $Mg(OR^1)_x X^1_{2-x}$, wherein: $R^4$ and $R_4'$ are the same as $R^1$ being a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms; $X^4$ and $X^1$ are each independently selected from the group of consisting of fluoride (F—), chloride (Cl—), bromide (Br—) or iodide (I—), preferably chloride; z is in a range of larger than 0 and smaller than 2, being 0<z<2;

ib) precipitating the solid $Mg(OR^1)_x X^1_{2-x}$ obtained in step i) by contacting it with an tetrahalogensilane, $SiX^{4'}_4$, wherein $X^{4'}$ is each independently selected from the group of consisting of fluoride (F—), chloride (Cl—), bromide (Br—) or iodide (I—), preferably chloride to obtain a solid support;

ii) optionally contacting the solid support obtained in step ib) with at least one activating compound selected from the group formed by activating electron donors and metal alkoxide compounds of formula $M^1(OR^2)_{v-w}(OR^3)_w$ or $M^2(OR^2)_{v-w}(R^3)_w$, to obtain a second intermediate reaction product; wherein: $M^1$ is a metal selected from the group consisting of Ti, Zr, Hf, Al or Si; $M^2$ is a metal being Si; v is the valency of $M^1$ or $M^2$; $R^2$ and $R^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms, and preferably has from 1 to 20 carbon atoms;

iii) contacting the first or second intermediate reaction product obtained in step ib) or ii) respectively, with a halogen-containing titanium compound and either an activator or an internal electron donor to obtain a third intermediate reaction product;

iv) optionally modifying the third intermediate reaction product obtained in step iii) with a modifier having the formula $MX_3$, wherein M is a metal selected from the Group 13 metals and transition metals of the IUPAC periodic table of elements, and wherein X is a halide, to yield a modified intermediate reaction product;

v) contacting said third intermediate reaction product obtained in step iii) or said modified intermediate reaction product obtained in step iv) with a halogen-containing titanium compound and in the case that in step iii) an activator was used an internal donor to obtain the procatalyst, wherein preferably step v) is carried out at least two times.

In an embodiment, the activator added during step iii) is selected from the group alkylbenzoate, benzamide, and monoester. In an embodiment, the activator added during step iii) is ethylbenzoate. In an embodiment, the alkyl magnesium compound used in step i) is dibutylmagnesium. In an embodiment, the Grignard reagent used in step i) is butyl magnesium chloride. In an embodiment, the compound of formula $R^4_z MgX^4_{2-z}$ used in step i), the halogen-containing titanium compound used in step iii) and step v) are used in such amounts that the resulting procatalyst comprises in wt. % based on the total weight of the procatalyst:magnesium: from 15 to 24, titanium: from 1 to 4. In an embodiment, the compound of formula $R^4_z MgX^4_{2-z}$ used in step i), the halogen-containing titanium compound used in step iii) and step v) are used in such amounts that the resulting procatalyst comprises in wt. % based on the total weight of the procatalyst:magnesium: from 18.0 to 19.5; titanium: from 1.5 to 3.5. In an embodiment, step ii) is carried out using a combination of an alcohol, preferably ethylalcohol, and a tetra alkoxy titanium compound, preferably tetra ethoxy titanium, as the activating compounds. In an embodiment, the ratio between the alkyl magnesium and Grignard reagent is between 1:1 and 1:4. In an embodiment, said tetrahalogensilane compound is present in respect of the amount of magnesium (in the form of alkyl magnesium and Grignard reagent) in a ratio of 0.2 to 5, preferably 0.5 to 1.

Another aspect relates to a procatalyst that is obtainable by the process according to the present invention. In an embodiment of said aspect, said procatalyst comprises a titanium catalyst supported on a solid magnesium-containing support wherein said procatalyst comprises in wt. % based on the total weight of the procatalyst:magnesium: from 15 to 24; titanium: from 1 to 4. In a further embodiment, said procatalyst comprises in wt. % based on the total weight of the procatalyst:magnesium: from 19.0 to 19.5; titanium: from 1.5 to 3.5.

Another aspect relates to a procatalyst comprising a titanium catalyst supported on a solid magnesium-containing support wherein said procatalyst comprises in wt. % based on the total weight of the procatalyst:magnesium: from 15 to 24; titanium: from 1 to 4.

Another aspect relates to a catalyst system suitable for olefin polymerization comprising the procatalyst according to the present invention or obtainable by the process according to the present invention and a co-catalyst and optionally an external electron donor. In an embodiment, the co-catalyst is an organometallic compound containing a metal from group 1, 2, 12 or 13 of the Periodic System of the Elements.

Another aspect relates to a process of preparing a polyolefin by contacting at least one olefin with a polymerization catalyst system according to the present invention.

In an embodiment, the olefin is propylene or a mixture of propylene and ethylene. In an embodiment, the olefin is a mixture of propylene and ethylene.

The present teachings moreover relate to a polyolefin obtained or obtainable by the process for preparing a polyolefin according to the present invention. In an embodiment thereof, said polyolefin is a homopolymer of propylene having a xylene solubles content of less than 2 wt. %. Moreover, in a different aspect the present invention relates to a homopolymer of propylene obtained or obtainable by the process for preparing a polyolefin according to the present invention having an xylene solubles content of less than 2 wt. %.

These aspects and embodiments will be described in more detail below.

DEFINITIONS

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound comprises Ziegler-Natta catalytic species, supported on a metal or metalloid compound (e.g. a magnesium compound or a silica compound).

"Ziegler-Natta catalytic species" or "catalytic species" as used in the present description means: a transition metal-containing species comprises a transition metal halide selected from titanium halide, chromium halide, hafnium halide, zirconium halide and vanadium halide, "internal donor" or "internal electron donor" or "ID" as used in the present description means: an electron-donating compound containing one or more atoms of oxygen (O) and/or nitrogen (N).

"external donor" or "external electron donor" or "ED" as used in the present description means: an electron-donating compound used as a reactant in the polymerization of olefins. It comprises at least one functional group that is capable of donating at least one pair of electrons to a metal atom.

"activator" as used in the present description means: an electron-donating compound containing one or more atoms of oxygen (O) and/or nitrogen (N) which is used to during the synthesis of the procatalyst prior to or simultaneous with the addition of an internal donor.

"activating compound" as used in the present description means: a compound used to activate the solid support prior to contacting it with the catalytic species.

"modifier" or "Group 13- or transition metal modifier" as used in the present description means: a metal modifier comprising a metal selected from the metals of Group 13 of the IUPAC Periodic Table of elements and transition metals. Where in the description the terms metal modifier or metal-based modifier is used, Group 13- or transition metal modifier is meant.

"procatalyst" and "catalyst component" as used in the present description have the same meaning: a component of a catalyst composition generally comprising a solid support, a transition metal-containing catalytic species and optionally one or more internal donor.

"halide" or "halogen" as used in the present description means: an ion selected from the group of: fluoride (F—), chloride (Cl—), bromide (Br—) or iodide (I—).

"Heteroatom" as used in the present description means: an atom other than carbon or hydrogen. However, as used herein—unless specified otherwise, such as below,—when "one or more hetereoatoms" is used one or more of the following is meant: F, Cl, Br, I, N, O, P, B, S or Si. Thus a heteroatom also includes halides. * "hydrocarbyl" as used in the present description means: is a substituent containing hydrogen and carbon atoms, or linear, branched or cyclic saturated or unsaturated aliphatic radical, such as alkyl, alkenyl, alkadienyl and alkynyl; alicyclic radical, such as cycloalkyl, cycloalkadienyl cycloalkenyl; aromatic radical, such as monocyclic or polycyclic aromatic radical, as well as combinations thereof, such as alkaryl and aralkyl. "substituted hydrocarbyl" as used in the present description means: is a hydrocarbyl group that is substituted with one or more non-hydrocarbyl substituent groups. A non-limiting example of a non-hydrocarbyl substituent is a heteroatom. Examples are alkoxycarbonyl (viz. carboxylate) groups. When in the present description "hydrocarbyl" is used it can also be "substituted hydrocarbyl", unless stated otherwise.

"alkyl" as used in the present description means: an alkyl group being a functional group or side-chain consisting of carbon and hydrogen atoms having only single bonds. An alkyl group may be straight or branched and may be un-substituted or substituted. An alkyl group also encloses aralkyl groups wherein one or more hydrogen atoms of the alkyl group have been replaced by aryl groups.

"aryl" as used in the present description means: an aryl group being a functional group or side-chain derived from an aromatic ring. An aryl group and may be un-substituted or substituted with straight or branched hydrocarbyl groups. An aryl group also encloses alkaryl groups wherein one or more hydrogen atoms on the aromatic ring have been replaced by alkyl groups.

"alkoxide" or "alkoxy" as used in the present description means: a functional group or side-chain obtained from an alkyl alcohol. It consist of an alkyl bonded to a negatively charged oxygen atom.

"aryloxide" or "aryloxy" or "phenoxide" as used in the present description means: a functional group or side-chain obtained from an aryl alcohol. It consist of an aryl bonded to a negatively charged oxygen atom.

"Grignard reagent" or "Grignard compound" as used in the present description means: a compound or a mixture of compounds of formula $R^4_z MgX^4_{2-z}$ ($R^4$, z, and $X^4$ are as defined below) or it may be a complex having more Mg clusters, e.g. $R_4Mg_3Cl_2$.

"polymer" as used in the present description means: a chemical compound comprising repeating structural units, wherein the structural units are monomers.

"olefin" as used in the present description means: an alkene.

"olefin-based polymer" or "polyolefin" as used in the present description means: a polymer of one or more alkenes.

"propylene-based polymer" as used in the present description means: a polymer of propylene and optionally a comonomer.

"polypropylene" as used in the present description means: a polymer of propylene.

"copolymer" as used in the present description means: a polymer prepared from two or more different monomers.

"monomer" as used in the present description means: a chemical compound that can undergo polymerization.

"thermoplastic" as used in the present description means: capable of softening or fusing when heated and of hardening again when cooled.

"Polymer composition" as used in the present description means: a mixture of either two or more polymers or of one or more polymers and one or more additives.

"MWD" or "Molecular weight distribution" as used in the present description means: the same as "PDI" or "polydispersity index". It is the ratio of the weight-average molecular weight (Mw) to the number average molecular weight ($M_n$), viz. $M_w/M_n$, and is used as a measure of the broadness of molecular weight distribution of a polymer. $M_w$ and $M_n$ are determined by GPC using a Waters 150° C. gel permeation chromatograph combined with a Viscotek 100 differential viscosimeter; the chromatograms were run at 140° C. using 1,2,4-trichlorobenzene as a solvent; the refractive index detector was used to collect the signal for molecular weights.

"XS" or "xylene soluble fraction" or "CXS" or "cold soluble xylene fraction" as used in the present description means: the weight percentage (wt. %) of soluble xylene in the isolated polymer, measured according to ASTM D 5492-10.

"polymerization conditions" as used in the present description means: temperature and pressure parameters within a polymerization reactor suitable for promoting polymerization between the catalyst composition and an olefin to form the desired polymer. These conditions depend on the type of polymerization used.

"production rate" or "yield" as used in the present description means: the amount of kilograms of polymer produced per gram of catalyst composition consumed in the polymerization reactor per hour, unless stated otherwise.

"bulk density" as used in the present description means: the mass of particles of the polymer divided by the total volume these particles occupy. It is measured according to ASTM D 1895.

Unless stated otherwise, when it is stated that any R group is "independently selected from" this means that when several of the same R groups are present in a molecule they may have the same meaning of they may not have the same meaning. For example, for the compound $R_2M$, wherein R is independently selected from ethyl or methyl, both R groups may be ethyl, both R groups may be methyl or one R group may be ethyl and the other R group may be methyl.

DETAILED DESCRIPTION OF THE INVENTION

The present invention is described below in more detail. All embodiments described with respect to one aspect are also applicable to the other aspects of the invention, unless otherwise stated. The present invention relates to a procatalyst and a method of preparing thereof; including the preparation of the magnesium support for said procatalyst without affecting the morphology and the particle size distribution of the solid support. In other words, the morphology and particle size distribution of a solid support prepared according to the present invention is similar to that prepared by a process as disclosed in EP2027164B1 as discussed above. The solid support of the procatalyst is prepared using a combination of alkyl magnesium and alkyl magnesium halide (Grignard reagent) whereas in the prior art only alkyl magnesium halide (Grignard reagent) is used.

As stated above, the procatalyst according to the present invention shows a higher bulk density, particularly with homo polypropylene and shows better isotacticity and a low xylene solubles content; due to the possibility of tuning the chloride content (e.g. increased) and ethoxide content (e.g. decreased). It is believed that the chloride content has an impact on the porosity of the support which in turn is believed to play an important role during the (co)-polymerization. Moreover, it is believed that as the amount of ethoxide in the procatalyst is reduced, the amount of titanium anchored is also reduced and hence the polymer obtained shows an increase in isotacticity.

The present invention aims at an easy manner to prepare said procatalyst using a process that requires no special set up or instruments (such as specially designed mini mixers).

The chloride content may for example vary from 20-50 wt. % in the support, preferably between 30 and 50 wt. %, more preferably between 35 and 45 wt. %. The chloride content in the procatalyst may for example vary from 50-85 wt. %, preferably between 50 and 75 wt. %, more preferably between 60 and 75 wt. %.

The ethoxide content may for example vary from 1-40 wt. % in the support, preferably between 5 and 30 wt. %. The ethoxide content in the procatalyst may for example vary from 0.005-4 wt. %, preferably between 0.01 and 2 wt. %, more preferably between 0.01 and 1.5 wt. %. the ethoxide content is tuned by the precipitation step using tetrahalogensilane.

The size (particle size distribution) and shape (morphology) of the catalyst particles are not affected and thus results in a high bulk density with low generation of fines.

In an aspect, the Ziegler-Natta type procatalyst in the catalyst system according to the present invention is obtained by the process that is similar to the process as described in Example I of EP2027164B1; the method to produce the solid support is different. Example I including all sub-examples (IA-IE) is incorporated into the present description. More details about the different embodiments are disclosed in paragraphs [0016] to [0089]. All these embodiments related to the process and products are incorporated by reference into the present description.

In the following part of the description the different steps and phases of the process for preparing the procatalyst will be discussed. The process for preparing a procatalyst according to an aspect comprises the following phases: Phase A): preparing a solid support for the procatalyst; this is the key phase according to the present invention; Phase B): optionally activating said solid support obtained in phase A) using one or more activating compounds to obtain an activated solid support; Phase C): contacting said solid support obtained in phase A) or said activated solid support in phase B) with a catalytic species wherein phase C) comprises one of the following: * contacting said solid support obtained in phase A) or said activated solid support in phase B) with a catalytic species and one or more internal donors to obtain an intermediate product; or * contacting said solid support obtained in phase A) or said activated solid support in phase B) with a catalytic species and an activator to obtain an intermediate product; and Phase D: optionally modifying said intermediate product obtained in phase C) wherein phase D) may comprise one of the following: * modifying said intermediate product obtained in phase C) with a Group 13- or transition metal modifier in case an internal donor was used during phase C), in order to obtain a procatalyst; or * modifying said intermediate product obtained in phase C) with a Group 13- or transition metal modifier and one or more internal donors in case an activator was used during phase C), in order to obtain a procatalyst.

The procatalyst thus prepared can be used in polymerization of olefins using an external donor and a co-catalyst. The various steps used to prepare the catalyst according to the present invention (and the prior art) are described in more detail below. The catalyst according to the present invention thus prepared can be used in polymerization of olefins using an external donor and a co-catalyst.

In a first specific embodiment, the process for preparing a procatalyst according to the present invention comprises phase A: preparing a solid support for the catalyst using a butyl Grignard and a butyl magnesium compound; phase B: activating said solid support for the catalyst; phase C: contacting said solid support with the catalytic species and an phthalate internal donor.

Phase A: Preparing a Solid Support for the Catalyst

A magnesium-containing support is used according to the present teaching. The step of preparing a support for the catalyst is modified in respect to prior art process. Synthesis of magnesium-containing supports, such as magnesium halides, alkyls, aryls, alkoxy- and aryloxy compounds for polyolefin (e.g. PP) production, are described for instance in U.S. Pat. No. 4,978,648, WO96/32427A1, WO01/23441 A1, EP1283222A1, EP1222214B1; U.S. Pat. Nos. 5,077,357; 5,556,820; 4,414,132; 5,106,806 and 5,077,357.

In an aspect, the process for preparing the solid support for the procatalyst comprises: step o) which is optional and step i). In step i) two compounds are used, being a Grignard reagent having the formula $R^4{}_z MgX^4{}_{2-z}$ and an alkyl magnesium compound having the formula $MgR^{4'}{}_2$ wherein: $R_4$ and $R_4'$ are each independently a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms. $R_4'$ is a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms. Preferably, both $R^{4'}$ groups are the same. Preferably, both $R^{4'}$ groups are butyl, more preferably n-butyl groups. $R^4$ can be an alkyl, aryl, aralkyl, alkoxide, phenoxide, etc., or mixtures thereof; examples are methyl, ethyl, n-propyl, i-propyl, n-butyl, i-butyl, t-butyl, hexyl, cyclohexyl, octyl, phenyl, tolyl, xylyl, mesityl, benzyl, phenyl, naphthyl, thienyl, indolyl. In an embodiment of the invention, $R^4$ represents an aromatic group, for instance a phenyl group. $X^4$ is selected from the group of consisting of fluoride (F—), chloride (Cl—), bromide (Br—) or iodide (I—). The value for z is in a range of larger than 0 and smaller than 2: $0<z<2$, e.g. between 0.5 and 1.5. The ratio between the alkyl magnesium and Grignard reagent may vary between 4:1 and 1:4, more preferably between 3:1 and 1:3, even more preferably between 2:1 and 1:3. Examples of ratios are 1:1 or 1:2 or 2:3. Preferably, the Grignard reagent is present in an amount that is equal or greater than the amount of alkyl magnesium. In case of an excess of alkyl magnesium this will lead to longer precipitation times which is undesirable.

Step o) Preparation of the Grignard Reagent (Optional)

The Grignard reagent used in step i) may be prepared by contacting metallic magnesium with an organic halide $R^4X^4$, as described in WO 96/32427 A1 and WO01/23441 A1. $R^4$ is as discussed above. All forms of metallic magnesium may be used, but preferably use is made of finely divided metallic magnesium, for example magnesium powder. To obtain a fast reaction it is preferable to heat the magnesium under nitrogen prior to use. Combinations of two or more organic halides $R^4X^4$ can also be used.

The magnesium and the organic halide $R^4X^4$ can be reacted with each other with or without the use of a separate dispersant; the organic halide $R^4X^4$ is used in excess when no dispersant is used. Examples of these dispersants are: aliphatic, alicyclic or aromatic dispersants containing from 4 up to 20 carbon atoms.

Preferably, in step o) an ether is added to the reaction mixture. Examples of ethers are: diethyl ether, diisopropyl ether, dibutyl ether, diisobutyl ether, diisoamyl ether, diallyl ether, tetrahydrofuran and anisole. Dibutyl ether and/or diisoamyl ether are preferably used. Preferably, an excess of chlorobenzene is used as the organic halide $R^4X^4$. Thus, the chlorobenzene serves as dispersant as well as organic halide $R^4X^4$. The organic halide/ether ratio acts upon the activity of the procatalyst. The chlorobenzene/dibutyl ether volume ratio may for example vary from 75:25 to 35:65, preferably from 70:30 to 50:50. Small amounts of iodine and/or alkyl halides can be added to cause the reaction between the metallic magnesium and the organic halide $R^4X^4$ to proceed at a higher rate. Examples of alkyl halides are butyl chloride, butyl bromide and 1,2-dibromoethane. When the organic halide $R^4X^4$ is an alkyl halide, iodine and 1,2-dibromoethane are preferably used.

The reaction temperature for step o) may be from 20 to 150° C.; the reaction time is normally from 0.5 to 20 hours. After the reaction for preparing $R^4_zMgX^4_{2-z}$ is completed, the dissolved reaction product may be separated from the solid residual products. The reaction may be mixed. The stirring speed can be determined by a person skilled in the art and should be sufficient to agitate the reactants.

Step i) Reacting Grignard Compound with Alkyl Magnesium and Silane Compound

Step i): contacting a compound $R^4zMgX^4_{2-z}$ and a compound $MgR^{4'}_2$— wherein $R^4$, $R^{4'}$, $X^4$, and z are as discussed above—with an alkoxy- or aryloxy-containing silane compound to give a first intermediate reaction product. Said first intermediate reaction product is a solid magnesium-containing support. In step i) a first intermediate reaction product is thus prepared by contacting the following reactants:

a Grignard reagent—being a compound or a mixture of compounds of formula $R^4_zMgX^4_{2-z}$; * a dialkyl magnesium compound; and * an alkoxy- or aryloxy-containing silane compound. Examples of these reactants are disclosed for example in WO 96/32427 A1 and WO01/23441 A1. The reactants disclosed therein are incorporated herein by reference.

Examples of suitable alkoxy- or aryloxy-containing silane compounds for use during step i) include compounds having at least one (preferably at least two, more preferably at least three, most preferably four) alkoxy or aryloxy group(s), such as methoxy, ethoxy, propoxy, butoxy, i-butoxy, t-butoxy or phenoxy and one or more combinations thereof. These compounds may also comprise one, two or three additional groups, such as alkyl groups, e.g. methyl, ethyl, propyl, butyl, i-butyl, t-butyl, phenyl etc. and one or more combinations thereof. Suitable non-limiting examples are provided below: tetramethoxysilane, tetraethoxysilane, tetrabutoxysilane, tetra-i-butoxysilane, tetraphenoxysilane, tetra(p-methylphenoxy)silane, tetrabenzyloxysilane, methyltrimethoxysilane, methyltriethyoxysilane, methyltributoxysilane, methyltriphenoxysilane, ethyltriethoxysilane, ethyltri-i-butoxysilane, ethyltriphenoxysilane, dimethyldiphenoxysilane, diphenyldimethoxysilane, butyltrimethoxysilane, butyltrietboxysilane, butyltributoxysilane, butyltriphenoxysilane, isobutyltriisobutoxysilane, vinyl triethyoxysilane, allyltriiethoxysilane, benzyltriphenoxysilane, methyltriallyloxysilane, dimethyldimethoxysilane, dimethyl-diethoxysilane, dimethyldiisopropyloxysilane, dimethyldibutoxysilane, dimethyl-dihexyloxysilane, diethyldiethoxysilane, diethyldiisobutoxysilane, diethyldiphenoxysilane, dibutyldiisopropyloxysilane, dibutyldibutoxysilane, dibutyldiphenoxysilane, diisobutyldiethoxysilane, diisobutyldiisobutoxysilane, diphenyldiethoxysilane, diphenyldibutoxysilane, dibenzyldiethoxysilane, divinyl diphenoxysilane, diallyldipropoxysilane, diphenyldiallyloxysilane, methylphenyldimethoxysilane, chlorophenyldiethyoxysilane, phenyltrimethoxy-silane, phenyltriethoxy-silane, diethyldiphenoxysilane, n-propyltriethoxysilane, diisopropyldi-methoxysilane, diisobutyldimethoxysilane, n-propyltrimethoxysilane, cyclohexylmethyldimethoxysilane, dicyclopentyldimethoxy-silane, isobutylisopropyldimethoxylsilane, phenyl-trimethoxysilane, diphenyl-dimethoxysilane, trifluoropropylmethyl-dimethoxysilane, bis(perhydroisoquinolino)-dimethoxysilane, dicyclohexyldimethoxy-silane, dinorbornyl-dimethoxysilane, di(n-propyl)dimethoxysilane, di(iso-propyl)-dimethoxysilane, di(n-butyl)dimethoxysilane and/or di(iso-butyl)dimethoxysilane, In an embodiment, as Grignard compound used in step i) a phenyl Grignard or a butyl Grignard is used (wherein $R_4$ is either phenyl or butyl and X is Cl and z is 1). A butyl Grignard is preferred when using a dibutyl magnesium since this will lead to a homogeneous system. In case a phenyl Grignard would be used together with a dibutyl magnesium, heterogeneity in the solid support would be obtained. Phenyl Grignard is more active than butyl Grignard. When butyl Grignard is used, an activation step using an aliphatic alcohol, such as methanol is preferably carried out in order to increase the activity. Such an activation step is not required with the use of phenyl Grignard. A phenyl Grignard might lead to benzene rest products and is more expensive. A butyl Grignard is benzene free and is commercially more interesting due to the lower price.

In the Grignard compound of formula $R^4_zMgX^4_{2-z}$ is preferably from about 0.5 to 1.5. The compound $R^4_zMgX^4_{2-z}$ may be prepared in an optional step (step o) which is discussed above), preceding step i) or may be obtained from a different process. The alkoxy- or aryloxy-containing silane used in step i) is preferably a compound or a mixture of compounds with the general formula $Si(OR^5)_{4-n}R^6_n$. Wherein it should be noted that the $R^5$ group is the same as the $R^1$ group. The $R^1$ group originates from the $R^5$ group during the synthesis of the first intermediate reaction product. $R^5$ is a hydrocarbyl group independently selected from alkyl, alkenyl, aryl, aralkyl, alkoxycarbonyl or alkylaryl groups, and one or more combinations thereof. More information regarding this $R^5$ group is as disclosed in WO2015091984 A1 of the same applicant, page 18, line 33 to page 19, line 9 which section is incorporated here by reference. $R^5$ is most preferably selected from ethyl and methyl. $R^6$ is a hydrocarbyl group independently selected from alkyl, alkenyl, aryl, aralkyl, alkoxycarbonyl or alkylaryl groups, and one or more combinations thereof. More information regarding this $R^6$ group is as disclosed in WO2015091984 A1 of the same applicant, page 19, lines 11-20 which section is incorporated here by reference. The value for n lies in the range of 0 up to 4, preferably n is from 0 up to and including 1. Examples of suitable silane compounds are as disclosed in WO2015091984 A1 of the same applicant, page 19, lines 25-33, which section is incorporated here by reference. Preferably, tetraethoxysilane is used as silane-compound in preparing the solid Mg-containing compound during step i) in the process according to the present invention.

Preferably, in step i) the silane-compound was introduced in to the Grignard compound kept in a well-stirred vessel at controlled temperature to result in particles of the first intermediate reaction product having advantageous morphology. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such procatalyst has a similar morphology as the procatalyst (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability.

As discussed above, the reactants are preferably introduced simultaneously. With "introduced simultaneously" is meant that the introduction of the Grignard compound and the silane-compound is done in such way that the molar ratio Mg/Si does not substantially vary during the introduction of these compounds. The silane-compound and Grignard compound can be continuously or batch-wise introduced to the mixing device. Preferably, both compounds are introduced continuously to a mixing device. The mixing device can have various forms; it can be a mixing device in which the silane-compound is premixed with the Grignard compound, the mixing device can also be a stirred reactor, in which the reaction between the compounds takes place. The separate components may be dosed to the mixing device by means of peristaltic pumps. Preferably, the compounds are premixed before the mixture is introduced to the reactor for step i). In this way, a procatalyst is formed with a morphology that leads to polymer particles with the best morphology (high bulk density, narrow particle size distribution, (virtually) no fines, excellent flowability).

The Si/Mg molar ratio during step i) may range from 0.2 to 20. Preferably, the Si/Mg molar ratio is from 0.5 to 1.0. The temperature during the premixing step of the reactants is not specifically critical, and may for instance range from 0 to 80° C.; preferably the temperature is from 10° C. to 50° C. The reaction between said reactants may, for instance, take place at a temperature from −20° C. to 100° C.; for example at a temperature of from 0° C. to 80° C. The reaction time is for example from 1 to 5 hours.

The mixing speed during the reaction depends on the type of reactor used and the scale of the reactor used. The mixing speed can be determined by a person skilled in the art. As a non-limiting example, mixing may be carried out at a mixing speed of from 250 to 300 rpm. In an embodiment, when a blade stirrer is used the mixing speed is from 220 to 280 rpm and when a propeller stirrer is used the mixing speed is from 270 to 330 rpm. The stirrer speed may be increased during the reaction. For example, during the dosing, the speed of stirring may be increased every hour by 20-30 rpm.

The first intermediate reaction product obtained by this step i) may comprise a compound of the formula $Mg(OR^1)_x X^1_{2-x}$, wherein: $R^1$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms. Most preferably selected from ethyl and methyl. $X^1$ is selected from the group of consisting of fluoride (F—), chloride (Cl—), bromide (Br—) or iodide (I—). Preferably, $X^1$ is chloride or bromine and more preferably, $X^1$ is chloride. The value for x is in the range of larger than 0 and smaller than 2: $0<z<2$. The value for x is preferably from 0.5 to 1.5.

The first intermediate reaction product obtained from the reaction between the silane compound, the alkyl magnesium compound and the Grignard compound is subsequently precipitated using a step ib) of precipitation.

Step ib)

The formation of $Mg(OR^1)_x X^1_{2-x}$ is completed by the precipitation thereof. This precipitation is effected by the addition of a tetrahalogensilane compound, preferably in the ratio of 0.2 to 5 to that of Mg and more preferably in the ratio of 0.5 to 1. This addition can for example be carried out at a temperature varying from 0 to 50° C. The addition preferably is carried out at 10° C. and then the solution is brought to 50° C. over a period of 10 minutes. After then, the resulting mixture is cooled, the solid is allowed to settle and afterwards the supernatant is decanted and the solid is washed with preferably an alkane, more preferably heptane, preferably at a temperature of 30 to 50° C. The solid product can be stored and further used as a suspension in said inert solvent. Alternatively, the product may be dried, preferably partly dried, and preferably under mild conditions; e.g. at ambient temperature and pressure.

Phase B: Activating Said Solid Support for the Catalyst

This step of activating said solid support for the catalyst is an optional step that is not required, but is preferred, in the present invention. If this step of activation is carried out, preferably, the process for activating said solid support comprises the following step ii). This phase may comprise one or more stages. Step ii) relates to the activation of the solid magnesium compound and this step, including many embodiments, is described in detail in WO2015091984 A1 of the same applicant, page 23 line 3 to page 28, line 14, which complete section is incorporated here by reference. According to the present invention, the solid support and procatalyst preferably have an average particle size distribution (or particle size distribution PDS) of between 24-30 microns. The particle size is measured using a test method based on ASTM standard test method D4464-201.

Phase C: Contacting Said Solid Support with the Catalytic Species and Either an Internal Donor or an Activator.

A detailed description of this phase is to be found in WO2015091984 A1 of the same applicant, page 28 line 15 to page 31 line 30, which complete section is incorporated here by reference.

Phase D: Optionally Modifying Said Catalyst with a Metal-Based Modifier.

This phase D is an optional step in the present invention. This phase discussed below can be completely omitted in the present invention. In an embodiment, this phase consists of the following steps: Step iv) modifying the third intermediate reaction product with a metal-modifier to yield a modified intermediate reaction product; and Step v) contacting said modified intermediate reaction product with a titanium halide and optionally an internal donor to obtain the present procatalyst. More information regarding this phase is described in WO2015091984 A1 of the same applicant, page 31 line 25 to page 32 line 27, which complete section is incorporated here by reference.

Step iv): Group 13- or Transition Metal Modification

This step relates to the modification with Group 13- or transition metal, preferably aluminum, this ensures the presence of Group 13- or transition metal in the procatalyst, in addition to magnesium (from the solid support) and titanium (from the titanation treatment). A detailed description of step iv) is to be found in WO2015091984 A1 of the same applicant, page 32 line 31 to page 35 line 11, which complete section is incorporated here by reference. Subsequent to this optional step, step v) is carried out to produce the procatalyst according to the present invention. In another embodiment, step v) is carried out directly after step iii) discussed above.

Step v): Titanation of Intermediate Product

This step is very similar to step iii). It contains the additional titanation of the intermediate product obtained in step iii) or step iv). Step v) contacting said third intermediate product obtained in step iii) or said modified intermediate product obtained in step iv) with a halogen-containing titanium compound to obtain the procatalyst according to the present invention. When an activator is used during step iii) an internal donor is used during this step. A detailed description of step v) is to be found in WO2015091984 A1 of the same applicant, page 35 line 26 to page 37 line 14, which is incorporated here by reference.

More information regarding e.g. the ratios of reaction products, weight ratio of certain components in the solid procatalyst and details regarding the procatalyst and its components are as described in WO2015091984 A1 of the same applicant (page 40 line 25 to page 41 line 23), which complete section is incorporated here by reference.

In an embodiment, an activator is present during this step iii). Preferably, no internal donor is added during this step when an activator is used. The activator is preferably an alkylbenzoate, more preferably ethylbenzoate. The activator may also be a monoester. When an activator is present during this step, an internal donor is added during step v) described below. Alkylbenzoates may be used as activators. A detailed description of regarding the use of alkylbenzoates as activators is to be found in WO2015091984 A1 of the same applicant, page 42 lines 1-12, which section is incorporated here by reference. Mono-esters may be used as activators. The monoester according to the present invention can be any ester of a monocarboxylic acid known in the art. A detailed description of regarding the use of mono-esters as activators is to be found in WO2015091984 A1 of the same applicant, page 42 line 14 to page 43 line 24, which section is incorporated here by reference.

The internal electron donor used in the procatalyst can be any compound known in the art to be used as internal electron donor. Suitable examples of internal donors include aromatic acid esters, such as monocarboxylic acid ester or dicarboxylic acid esters (e.g. ortho-dicarboxylic acid esters such as phthalic acid esters), (N-alkyl)amidobenzoates, 1,3-diethers, silyl esters, fluorenes, succinates and/or combinations thereof.

In an aspect, the internal donor used during step iii) or step v) is selected from the group consisting of dicarboxylic acid esters (phthalates). A detailed description of regarding the use an internal donor selected from the group consisting of dicarboxylic acid esters (phthalates) during step iii) or step v) is to be found in WO2015091984 A1 of the same applicant, page 44 line 4 to page 45 line 8, which is incorporated here by reference.

When an aminobenzoate (AB) according to Formula XI of WO2015091984 A1 of the same applicant is used as an internal donor this ensures a better control of stereochemistry and allows preparation of polyolefins having a broader molecular weight distribution. A detailed description of regarding the use of an aminobenzoate (AB) as an internal donor is to be found in WO2015091984 A1 of the same applicant, page 45 line 10 to page 53 line 6, which is incorporated here by reference. Preferably, the aminobenzoate is 4-[benzoyl(methyl)amino]pentan-2-yl benzoate:

Other suitable internal donors, such as benzoic acid esters (monocarboxylic aromatic esters), 1,3-di-ethers, succinate acid esters, silyl esters and other organic compounds are those described in WO2015091984 A1 of the same applicant, page 53 line 12 to page 58 line 15, which complete section is incorporated here by reference_or one or more combination thereof, or in combination with the preferred internal donors cited above.

The process according to the present invention results in procatalysts, which allow obtaining polyolefins in a high yield and with a high polymer bulk density. The invention further relates to a procatalyst for polymerization of olefins obtained or obtainable by the process according to the invention. The invention also relates to a catalyst system that comprises the procatalyst according to the invention and a co-catalyst. Preferably, the catalyst system also comprises an external electron-donating compound, also referred to as external electron donor, or simply external donor. The catalyst system according to the present invention includes a co-catalyst. As used herein, a "co-catalyst" is a term well-known in the art in the field of Ziegler-Natta catalysts and is recognized to be a substance capable of converting the procatalyst to an active polymerization catalyst. Generally, the co-catalyst is an organometallic compound containing a metal from group 1, 2, 12 or 13 of the Periodic System of the Elements (Handbook of Chemistry and Physics, 70th Edition, CRC Press, 1989-1990). The co-catalyst may include any compounds known in the art to be used as "co-catalysts", as described in WO2015091984 A1 of the same applicant, page 59 line 1 to page 60 line 30, which is incorporated here by reference.

One of the functions of an external donor compound is to affect the stereoselectivity of the catalyst system in polymerization of olefins having three or more carbon atoms. Therefore it may be also referred to as a selectivity control agent. Examples of external donors suitable for use in the present invention are the internal donors benzoic acid esters and 1,3-diethers. In addition, the following external donors may be used: alkylamino-alkoxysilanes, alkyl-alkoxysilane, imidosilanes, and alkylimidosilanes. The aluminum/external donor molar ratio in the polymerization catalyst system preferably is from 0.1 to 200; more preferably from 1 to 100. Mixtures of external donors may be present and may include from about 0.1 mol. % to about 99.9 mol. % of a first external donor and from about 99.9 mol. % to about 0.1 mol. % of either a second or the additional alkoxysilane external donor disclosed below. When a silane external donor is used, the Si/Ti molar ratio in the catalyst system can range from 0.1 to 40, preferably from 0.1 to 20, even more preferably from 1 to 20 and most preferably from 2 to 10.

Documents EP1538167 and EP1783145 disclose a Ziegler-Natta catalyst type comprising an organo-silicon compound as external donor that is represented by formula $Si(OR^c)_3(NR^dR^e)$, wherein $R^c$ is a hydrocarbon group having 1 to 6 carbon atoms, $R^d$ is a hydrocarbon group having 1 to 12 carbon atoms or hydrogen atom, and $R^e$ is a hydrocarbon group having 1 to 12 carbon atoms used as an external electron donor. Examples of suitable external donors according to the present invention are known from WO2015091984 A1, being compounds according to Formula III, alkyl-alkoxysilanes according to Formula IV, organosilicon compounds having formula $Si(OR^a)_{4-n}R^b{}_n$, imidosilanes according to Formula I, alkylimidosilanes according to Formula I' as described on page 61 line 26 to page 67 line 8 which is incorporated here by reference. Alkoxy silane halide are used for preparing imidosilane and alkylimidosilane internal donors and are, respectively, according to Formula XXIVa: $Z_nSi(OR^{11})_{4-n}$ and Formula XXIVa: $Z_nSi(OR^{11})_{4-n-m}(R^{12})_m$. In the alkoxy silane halide represented by Formula XXIVa and XXIVb, Z is halogen group, and more preferably a chlorine group; n=1, 2 or 3. Specific examples regarding the external donor, considering Formula I' in WO2015091984 A1, are described in WO2015091984 A1 of the same applicant, page 67 lines 9-22, which is incorporated here by reference.

The additional compound(s) in the external donor according to the invention may be one or more alkoxysilanes, as described in WO2015091984 A1 of the same applicant, page 67 line 24 to page 69 line 4, which section is incorporated here by reference. In an embodiment, the silane-compound for the additional external donor is dicyclopentyl dimethoxysilane, di-isopropyl dimethoxysilane, di-isobutyl dimethyoxysilane, methylcyclohexyl dimethoxysilane, n-propyl trimethoxysilane, n-propyltriethoxysilane, dimethylamino triethoxysilane, and one or more combinations thereof. Preferably, the external donor is an alkyl-alkoxysilane according to formula IV (preferably n-propyl trimethoxysilane or n-propyl triethoxysilane) or cyclohexylmethyldimethoxysilane or another dialkyldialkoxysilane.

The invention also relates to a process to make the catalyst system by contacting a Ziegler-Natta type procatalyst, a co-catalyst and an external electron donor. The procatalyst, the co-catalyst and the external donor can be contacted in any way known to the skilled person in the art; and as also described herein, more specifically as in the Examples. The invention further relates to a process of preparing a polyolefin by contacting at least one olefin with a polymerization catalyst system comprising the procatalyst according to the present invention. Preferably, the polyolefin made by using the catalyst system of the present invention is a polypropylene. It is an advantage of the present invention that polyolefins are obtained in a higher yield than when non-modified prior art procatalysts are used.

For instance, the external donor in the catalyst system according to the present invention can be complexed with the co-catalyst and mixed with the procatalyst (pre-mix) prior to contact between the catalyst composition and the olefin. The external donor can also be added independently to the polymerization reactor. The procatalyst, the cocatalyst, and the external donor can be mixed or otherwise combined prior to addition to the polymerization reactor. Contacting the olefin with the catalyst system according to the present invention can be done under standard polymerization conditions, known to the skilled person in the art. See for example Pasquini, N. (ed.) "Polypropylene handbook" $2^{nd}$ edition, Carl Hanser Verlag Munich, 2005. Chapter 6.2 and references cited therein. The polymerization process may be a gas phase, a slurry or a bulk polymerization process, operating in one or more than one reactor. One or more olefin monomers can be introduced in a polymerization reactor to react with the catalyst composition and to form an olefin-based polymer (or a fluidized bed of polymer particles). Polymerization in a slurry (liquid phase) as well as information about the polyolefins that are/may be prepared are described in WO2015091984 A1 of the same applicant, page 70 line 15 to page 71 line 23 which section is incorporated here by reference; information about gas-phase polymerization processes are as described in WO2015091984 A1 of the same applicant, page 71 line 25 to page 72 line 26 which is incorporated here by reference.

The olefin according to the invention may be selected from mono- and di-olefins containing from 2 to 40 carbon atoms; see also WO2015091984 A1 of the same applicant, page 72 line 28 to page 73 line 5 which section is incorporated here by reference. Preferably, the olefin is propylene or a mixture of propylene and ethylene, to result in a propylene-based polymer, such as propylene homopolymer or propylene-olefin copolymer. The olefin may an alpha-olefin having up to 10 carbon atoms, such as ethylene, butane, hexane, heptane, octene; more information regarding the polymers formed is as disclosed in WO2015091984 A1 of the same applicant, page 73 lines 6-23 which section is incorporated here by reference. The present invention also relates to a polyolefin, preferably a polypropylene obtained or obtainable by a process, comprising contacting an olefin, preferably propylene or a mixture of propylene and ethylene with the procatalyst according to the present invention; more information regarding the polymers formed is as disclosed in WO2015091984 A1 of the same applicant, page 73 lines 25-34 which section is incorporated here by reference. The present invention also relates to a polyolefin, preferably a propylene-based polymer obtained or obtainable by a process as described herein above, comprising contacting propylene or a mixture of propylene and ethylene with a catalyst system according to the present invention. In one embodiment the present invention relates to the production of a homopolymer of polypropylene. For such a polymer, properties such as isotacticity and stiffness and emission may be important.

The polyolefin, preferably the polypropylene, according to the present invention has a molecular weight distribution higher than 3.5, preferably higher than 4, more preferably higher than 4.5 and for instance below 10 or below 9 or even below 6. The molecular weight distribution of the polyolefins, preferably polypropylene according to the present invention is for instance from 3.5 to 9, preferably from 4 to 6, more preferably from 4.5 to 6. Xylene soluble fraction (XS) is preferably from about 0.5 wt. % to about 5 wt. %, or from about 1 wt. % to about 4 wt. %, or from 1.5 to 3.5 wt. %, or from about 1.8 wt. % to about 3 wt. %. Preferably, the xylene amount (XS) is lower than 5 wt. %, preferably lower than 4 wt. %, more preferably lower than 3.5 wt. % or even lower than 3 wt. % and most preferably lower than 2.7 wt. % or even lower than 2 wt. %. The present inventor have shown that the amount of xylene solubles can be reduced from 4-5% for a procatalyst according to the prior art to as low as 2 wt. % for a procatalyst according to the invention. This is elucidated in the Examples. Without wishing to be bound by any particular theory, it is proposed by the inventors that the present procatalyst comprises a reduced ethoxide content which is turn is responsible for the reduction in the amount of xylene solubles. Higher ethoxide leads to the formation of atactic site due to less electronegativity of the active metal center. This active metal center binds with the electron donor effectively to produce highly isotactic polymer, which is quite feasible with reduced amounts of ethoxide content. The ethoxide content according to the present invention can be tuned. The higher the chloride content (e.g. by increase the amount of tetrahalogensilane used) the lower the ethoxide content. The isotacticity is preferably at least 95%, more preferably at least 96%, even more preferably at least 97%, most preferably at least 98%. The present inventor have shown that the isotacticity, e.g. of a homopolymer of propylene, can be increased from 96% for a procatalyst according to the prior art to a value between 97% and 98% for a procatalyst according to the invention. This is elucidated in the Examples. The production rate is preferably from about 1 kg/gram/hour to about 100 kg/gram/hour, or from about 10 kg/gram/hour to about 40 kg/g/hr. More information regarding the olefin polymer obtained is as described in WO2015091984 A1 of the same applicant, page 74, line 26 to page 75, line 23.

The invention also relates to the use of the polyolefins, preferably the propylene-based polymers (also called polypropylenes) according to the invention in injection molding, blow molding, extrusion molding, compression molding, casting, thin-walled injection molding, etc. for example in food contact applications. Furthermore, the invention relates to a shaped article comprising the polyolefin, preferably the propylene-based polymer according to the present invention. The polyolefin, preferably the propylene-based polymer according to the present invention may be transformed into shaped (semi)-finished articles using a variety of processing techniques. Examples thereof are as described in WO2015091984 A1 of the same applicant, page 76, lines 1-10.

It is noted that the invention relates to all possible combinations of features recited in the claims. Features described in the description may further be combined. Although the invention has been described in detail for purposes of illustration, it is understood that such detail is solely for that purpose and variations can be made therein by those skilled in the art without departing from the spirit and scope of the invention as defined in the claims. The term 'comprising' does not exclude the presence of other elements; a product comprising certain components also discloses a product consisting of these components; a process comprising certain steps also discloses a process consisting of these steps. The invention will be further elucidated with the following examples without being limited hereto.

EXAMPLES

Several procatalysts according to the invention and comparative procatalysts not according to the invention were prepared. The first step is the preparation of the support, optionally the support is activated and subsequently the procatalyst is prepared. Productivity of polymerization is expressed as kilogram of polymer isolated per gram of catalyst after 60 minutes of polymerization time. (kg of PP formed per gram of catalyst per hour).

Support Preparation According to the Invention

A solution of $Bu_2Mg$ (1M, 50 mL) in heptane was concentrated to remove heptane at a temperature of 60° C. under a nitrogen atmosphere until a viscous yellow mass was formed. The yellow mass solidified upon cooling. To said solidified mass di-butyl ether was added to prepare a solution of $Bu_2Mg$ (1M) in dibutyl-ether. The resulting solution of $Bu_2Mg$ was mixed with a solution of BuMgCl (1M, 50 mL for Support 1a, 75 mL for Support 2a, and 100 mL for Support 3a) in a ratio of 1:1 for Support 1a and in a ratio of 2:3 for Support 2a and in a ratio of 1:2 for Support 3a. The addition mode of butyl magnesium chloride to butyl magnesium was kept slow in order to avoid any precipitation. This mixture was then added to 15 mL of a solution of $Si(OEt)_4$ in 50 mL dibutyl-ether at 5° C. The resulting clear yellow solution was allowed to stir at 5° C. during the addition. Then the solution was allowed to warm up to 25° C. and the solution was stirred for an additional 30 minutes. The temperature was then raised to 60° C. and the reaction mixture was kept for 1 hour. After that the reactants were cooled to 5° C. and during step ib) $SiCl_4$ (15 mL for Support 1a and 10 mL for Support 2a and 3a) in 50 mL dibutyl-ether was added slowly and the reaction mixture was stirred at 25° C. for 30 minutes followed by 2 hours stirring at 60° C. Then, the reaction mixture was allowed to cool and the supernatant liquid was decanted at 30° C. and the precipitate was washed with heptane at 50° C. and finally with isopentane at 25° C. Support 1a or 2a or 3a was obtained.

Support Preparation not According to the Invention

A magnesium support was prepared according to steps A and B of Example II of EP2027164B1 with the exception that butyl Grignard is used instead of phenyl Grignard. Support 4a was obtained.

Activation of Support According to the Invention and not According to the Invention In an inert nitrogen atmosphere at 0° C., a 250 ml glass flask equipped with a mechanical agitator was filled with slurry of 5 g of reaction product of support preparation (either Support 1a, 2a, 3a or 4a) dispersed in 60 ml of heptane. Subsequently, a solution of 1.0 ml ethanol in 20 ml of heptane was added at 0° C. resulting in a ratio ethanol/Mg:0.45. After keeping the reaction mixture at 0° C., for 30 minutes, a solution of 0.79 ml titanium tetraethoxide (TET/Mg:0.1) in 20 ml of heptane was added at 0° C. over a period of 1 hour. Then the resulting slurry was slowly heated to 30° C. over a period of 90 min and kept at that temperature for another 2 hours. Finally, the supernatant liquid was decanted from the solid reaction product (about 5.5 g), which was washed once with 90 ml of heptane at 30° C. The slurry was kept at 30° C. for another 2 hours. The supernatant liquid was decanted from the solid substance (about 5.5 g), which was washed once with 80 ml of heptane at 30° C. As a result, activated support 1, 2 or 3 or not according to the invention 4 was obtained, suspended in 15 ml of heptane.

Preparation of the Procatalyst

A reactor was brought under nitrogen and 125 ml of titanium tetrachloride was added to it. The reactor was heated to 115° C. and a suspension, containing about 5.5 g of Support 1a, in 15 ml of heptane, was added to it under stirring. Then the reaction mixture was kept at 115° C. for 15 min and 2.4 ml of di-n-butyl phthalate as internal donor was added to reactor. Then the reaction mixture was kept at 115° C. for 105 min. Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The reaction mixture was kept at 115° C. for 30 min, after which the solid substance was allowed to settle, and the last treatment was repeated once again. The solid substance obtained was washed five times using 150 ml of heptane at 60° C., after which the procatalyst I, suspended in heptane, was obtained. For Example II (E-II) Support 2a was used to prepare procatalyst II. For Example III (E-III) Support 3a was used to prepare procatalyst III. For Example IV (E-IV) activated Support 1 was used to prepare procatalyst IV. For Example V (E-V) activated Support 2 was used to prepare procatalyst V. For Example VI (E-VI) activated Support 3 was used to prepare procatalyst VI.

Comparative Examples I and II (C-I and C-II):
Preparation of Procatalyst VII and VIII Support 4 was used to prepare procatalyst VII. Activated support 4 was used to prepare procatalyst VIII. A procatalyst was prepared according to step D of Example II of EP2027164B1. Procatalyst VII or VIII is obtained.

Figure 1:
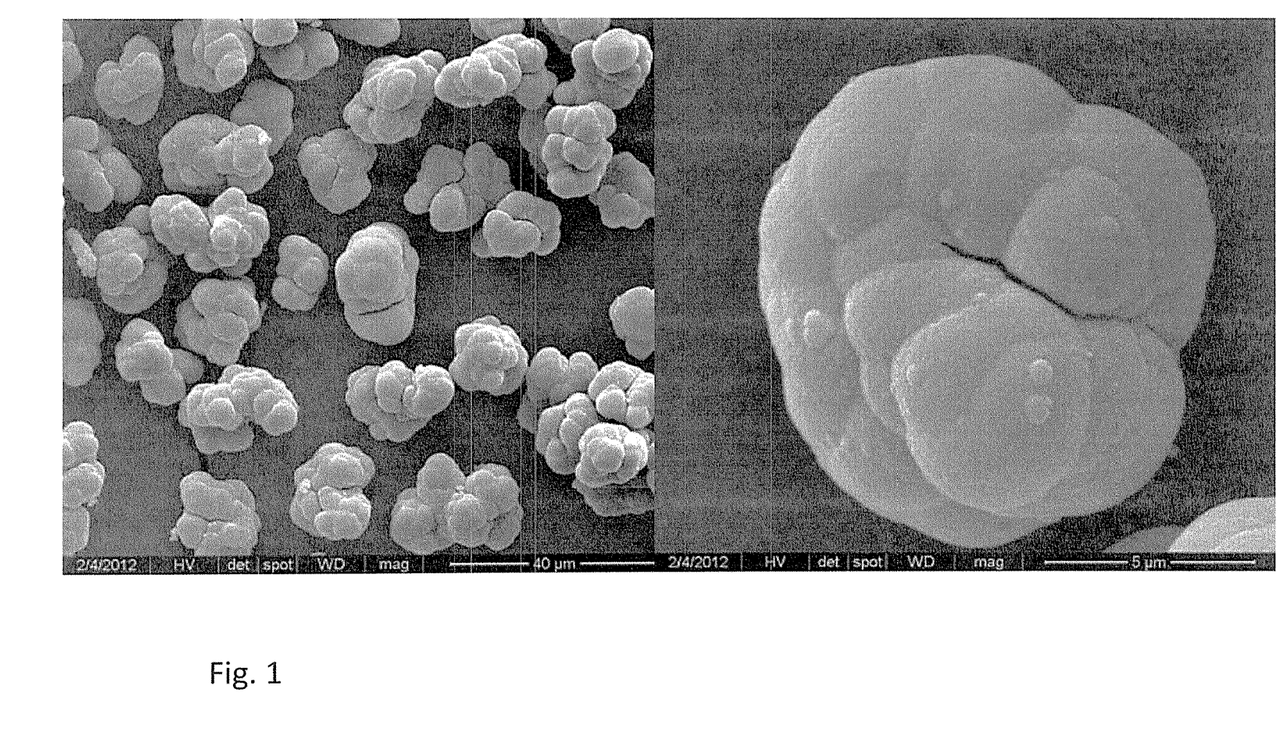
FIG. 1 shows SEM photographs of an embodiment of a procatalyst according to the present invention. On the right side an enlargement is shown of the photo on the left side.
Figure 2:
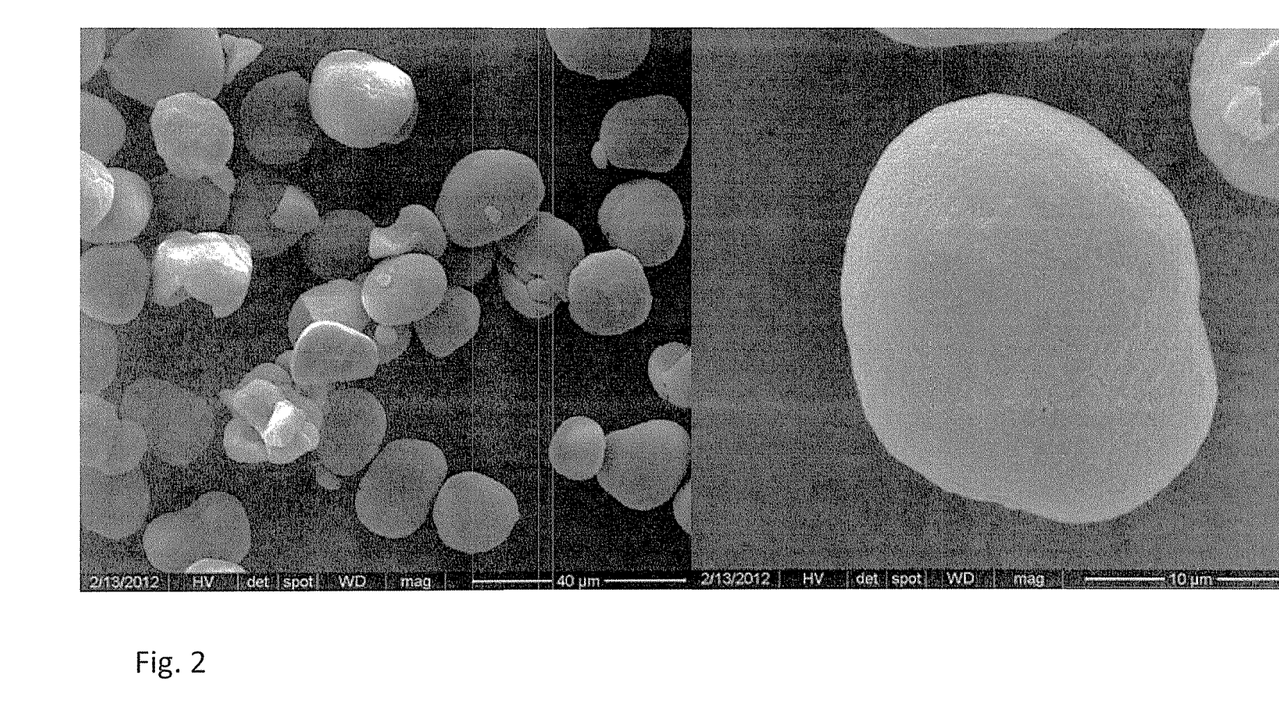
FIG. 2 shows SEM photographs of an embodiment of a procatalyst according to the present invention. On the right side an enlargement is shown of the photo on the left side.
Figure 3:
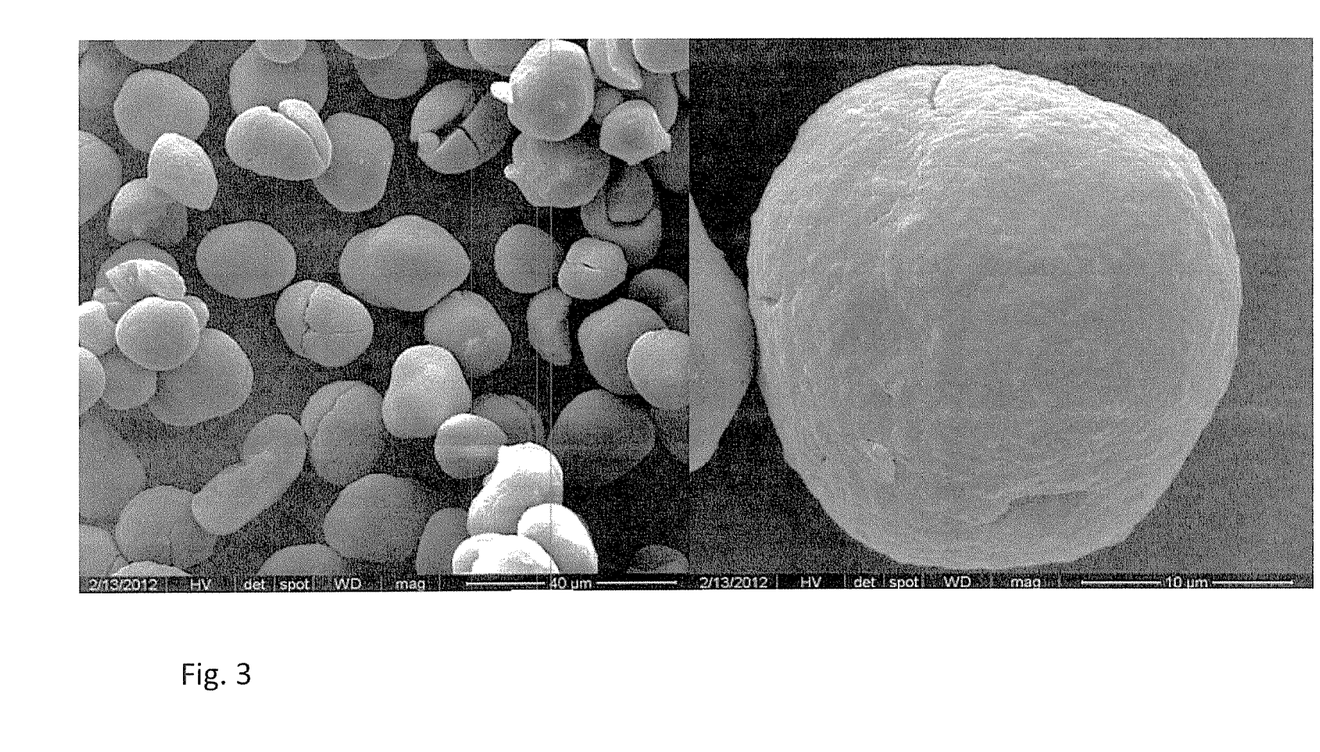
FIG. 3 shows SEM photographs of an embodiment of a procatalyst according to the present invention. On the right side an enlargement is shown of the photo on the left side.
Figure 4:
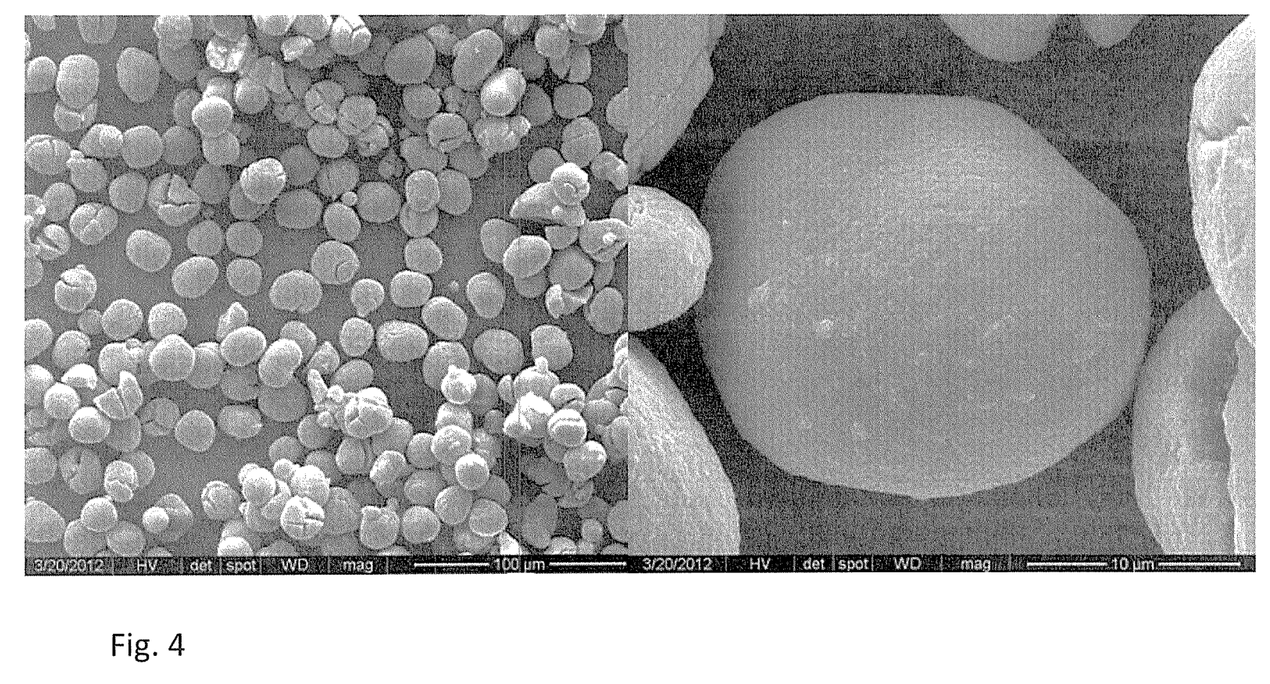
FIG. 4 shows SEM photographs of an embodiment of a procatalyst according to the present invention. On the right side an enlargement is shown of the photo on the left side.
Figure 5:
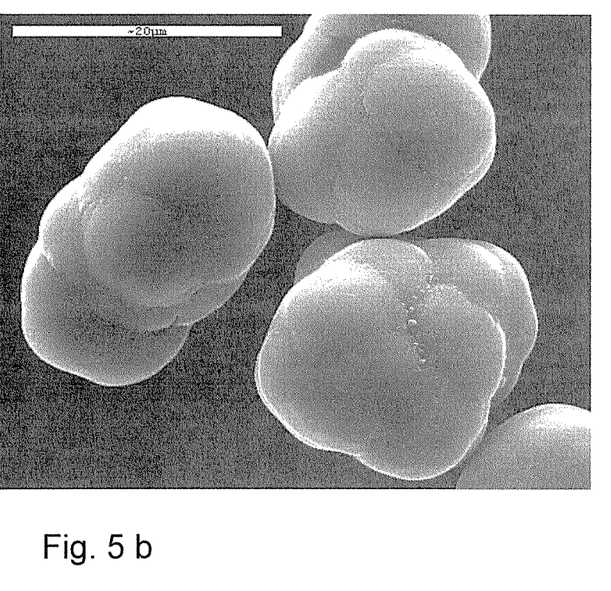
FIG. 5 shows SEM photographs showing the morphology of an activated support (FIG. 5A) and a non-activated support (FIG. 5B).

Information about the procatalysts I-VIII is disclosed in Table 1. The columns disclose the following: first=Example number; second=ratio of Bu$_2$Mg to BuMgCl (the comparative example uses alkyl magnesium so ratio is not applicable); third=amount of SiCl$_4$; fourth=magnesium content of (activated) support in wt. %; fifth=chloride content of the (activated) support in wt. %; sixth=ethoxide content of the (activated) support in wt. % (measured according to GC measurements using internal standard method); 4$^{th}$-6$^{th}$ all based on the weight of the support; seventh=activation step of support or not; eighth=chloride content of the resulting procatalyst in wt. %; ninth=titanium content of the resulting procatalyst in wt. %; tenth=ethoxide content of the resulting procatalyst in wt. %; 8$^{th}$-10$^{th}$ all based on the weight of the procatalyst. As an internal donor, di-n-butylphthalate (DNBP) is used. The support and procatalyst both show an average particle size distribution (or particle size distribution PDS) of between 24-30 microns. The particles of the polymer powder obtained had a round shape. The morphology of the support is similar as the activated support as is evidenced by the FIGS. 1-4. FIG. 1 shows a SEM photograph of procatalyst I (E-I); FIG. 2 of procatalyst IV (E-IV); FIG. 3 of procatalyst V (E-V); and FIG. 4 of procatalyst VI (E-VI). FIG. 5 shows that the morphology of an activated support according to comparative Example C-Ill (FIG. 5A) is very similar to the morphology of a non-activated support according to comparative Example C-I (FIG. 5B).

isotacticity. Procatalyst having a support according to the prior art have an isotacticity as high as 96%. With the present invention, a value as high as 97-98% can be obtained. This is significantly higher. With a procatalyst according to the present teachings it is possible to a polymer having a low xylene solubles value. Values for procatalyst having a standard support are between 4 and 6% whereas with the present invention values below 1.5% are obtained due to the activation of the support and the high ethoxide content of the support according to the present invention. The ethoxide content according to the present invention can be tuned.

Random Copolymerization of Ethylene and Propylene

Co-polymerization of propylene and ethylene was carried out in a stainless steel reactor (with a volume of 3 l) in propylene (1.375 kg), 40-200 g of ethylene at a temperature of 67° C., total pressure 24 bar and hydrogen presence (200 psi) for 1 hour in the presence of a catalyst system comprising the procatalyst (IV to VI), triethylaluminum (TEAL as the co-catalyst) and cyclohexylmethyldimethoxysilane (as the external electron donor which is a so-called C-donor or carbon donor). The amount of the procatalyst used was 0.025 g, the amount of triethylaluminum was 2.0 mmol and the concentration of cyclohexylmethyldimethoxysilane was 50 μl. Table 3 summarizes the results of the polymer products obtained in the polymerization.

It was found that the polyolefin produced using said catalyst has a high density and a good sensitivity for ethylene incorporation for the production of random polypropylene.

TABLE 1

| Ex. | Bu$_2$Mg:BuMgCl ratio | SiCl$_4$ (ml) | Mg support (wt. %) | Cl support (wt. %) | Ethoxide support (wt. %) | Activation | Cl Procat. (wt. %) | Ti Procat. (wt. %) | Ethoxide Procat. (wt. %) |
|---|---|---|---|---|---|---|---|---|---|
| E-I | 1:1 | 15 | 17.24 | 48 | 6.2 | No | 75 | 0.86 | 0.02 |
| E-IV | 1:1 | 15 | 17.14 | 45 | 7.6 | Yes | 74 | 0.98 | 0.02 |
| E-II | 2:3 | 10 | 18.46 | 42 | 14.2 | No | 72 | 1.34 | 0.74 |
| E-V | 2:3 | 10 | 18.26 | 41 | 16.1 | Yes | 65 | 1.38 | 0.98 |
| E-III | 1:2 | 10 | 18.42 | 36 | 24.5 | No | 58 | 2.02 | 1.2 |
| E-VI | 1:2 | 10 | 18.22 | 35 | 26.3 | Yes | 60 | 2.12 | 1.3 |
| C-I | n.a. | 0 | 20.16 | 64 | 31 | No | 62 | 2.21 | 1.1 |
| C-II | n.a. | 0 | 21.2 | 55 | 36 | Yes | 56 | 2.32 | 0.8 |

Polymerization of Propylene

Polymerization of propylene was carried out in a stainless steel reactor (with a volume of 3 liter) in propylene (1.375 kg) at a temperature of 67° C., with total pressure 24 bar and hydrogen presence (200 psi) for 1 hour in the presence of a catalyst system comprising the procatalyst (I to VI), triethylaluminum (TEAL as the co-catalyst) and cyclohexylmethyldimethoxysilane (as the external electron donor which is a so-called C-donor or carbon donor). The amount of the procatalyst used was 0.024 g, the amount of triethylaluminum was 2.0 mmol and the concentration of cyclohexylmethyldimethoxysilane was 50 μl for all experiments. Table 2 summarizes the results of the polymer products obtained in the polymerization.

With a procatalyst according to the present teachings it is possible to obtain polymers having a high bulk density. This can be obtained by increasing the titanium content, which can be tuned by the ethoxide content. An increase in the ethoxide content leads to an increase in the titanium content. The ethoxide content can be tuned by the correct selection of the amount of tetrahalogensilane during the precipitation of the support. With a procatalyst according to the present teachings it is possible to obtain polymers having a high

TABLE 2

| Run | Procatalyst | Procatalyst (mg) | TEAL mmol | Activity (Kg PP/ g cat) | XS (wt %) | Bulk density (g/ 100 ml) | Isotacticity (%) |
|---|---|---|---|---|---|---|---|
| 1 | I | 55 | 2 | 6.4 | 0.5 | 34.6 | 98.2 |
| 2 | I | 57 | 4 | 9.1 | 1.3 | 37.2 | n.d. |
| 3 | IV | 50 | 2 | 7.2 | 0.7 | 33.8 | 98.1 |
| 4 | IV | 48 | 4 | 12.4 | 1.2 | 36.5 | n.d. |
| 5 | II | 46 | 2 | 11.6 | 0.7 | 41.2 | 98.4 |
| 6 | II | 37 | 4 | 11.2 | 0.9 | 40.7 | n.d. |
| 7 | V | 35 | 2 | 19.4 | 1.1 | 43.1 | 97.8 |
| 8 | V | 36 | 4 | 21.3 | 1.2 | 41.8 | n.d. |
| 9 | III | 22 | 2 | 20.1 | 1.4 | 40.7 | 97.9 |
| 10 | III | 24 | 4 | 20.5 | 1.5 | 41.4 | n.d. |
| 11 | VI | 23 | 2 | 21.5 | 1.2 | 42.5 | 97.5 |
| 12 | VI | 24 | 4 | 22.8 | 1.4 | 42.2 | n.d. |
| 13 | VII | 20 | 2 | 18.1 | 5.4 | 40.2 | 93.2 |
| 14 | VII | 20 | 4 | 20.1 | 5.5 | 40.8 | n.d. |
| 15 | VIII | 20 | 2 | 28.2 | 4.1 | 42.1 | 96.1 |
| 16 | VIII | 20 | 4 | 30.1 | 5.5 | 41.0 | 94.1 |

TABLE 3

| Run | Catalyst (mg) | TEAL (mmol) | Amount ethylene [$C_2$ (g)] | Activity (Kg PP/g cat) | Ethylene incorpor. [E in (%)]* by NMR | Bulk density (g/100 ml) |
|---|---|---|---|---|---|---|
| 17 | IV (50) | 2 | 40 | 12.2 | 0.5 | 32.6 |
| 18 | IV (48) | 2 | 100 | 14.4 | 1.6 | 35.4 |
| 19 | V (35) | 2 | 100 | 21.4 | 1.7 | 40.4 |
| 20 | V (36) | 2 | 150 | 21.8 | 2.1 | 41.2 |
| 21 | VI (23) | 2 | 100 | 22.0 | 2.6 | 40.2 |
| 22 | VI (24) | 2 | 150 | 23.8 | 3.8 | 40.5 |
| 23 | VI (24) | 2 | 200 | 24.1 | 5.2 | 40.1 |
| 24 | VII (20) | 2 | 200 | 21.2 | 2.1 | 40.5 |
| 25 | VIII (20) | 2 | 200 | 33.1 | 2.4 | 42.1 |

The invention claimed is:

1. A process for preparing a procatalyst for preparing a catalyst composition for olefin polymerization, said process comprising the steps of:
    ia) contacting a Grignard reagent comprising $R^4{}_z MgX^4{}_{2-z}$ and an alkyl magnesium compound $MgR^{4'}{}_2$ with an alkoxy- or aryloxy-containing silane compound to give a first intermediate reaction product, being a solid $Mg(OR^1)_x X^1{}_{2-x}$, wherein:
        $R^4$ and $R_4{}'$ are the same as $R^1$ being a linear, branched or cyclic hydrocarbyl group independently selected from the group consisting of alkyl, alkenyl, aryl, aralkyl, alkoxycarbonyl, alkylaryl groups, and one or more combinations thereof; wherein said hydrocarbyl group is substituted or unsubstituted, and optionally contains one or more heteroatoms;
        $X^4$ and $X^1$ are each independently selected from the group consisting of fluoride (F—), chloride (Cl—), bromide (Br—) or iodide (I—);
        x is in a range of larger than 0 and smaller than 2, being $0<x<2$; and
        z is in a range of larger than 0 and smaller than 2, being $0<z<2$;
    ib) precipitating the solid $Mg(OR^1)_x X^1{}_{2-x}$ obtained in step ia) by contacting it with an tetrahalogensilane, $SiX^{4'}{}_4$, wherein $X^{4'}$ is each independently selected from the group consisting of fluoride (F—), chloride (Cl—), bromide (Br—) or iodide (I—), to obtain a solid support;
    ii) optionally contacting the solid support obtained in step ib) with at least one activating compound selected from the group consisting of activating electron donors and metal alkoxide compounds of formula $M^1(OR^2)_{v-w}(OR^3)_w$ and $M^2(OR^2)_{v-w}(R^3)_w$, to obtain a second intermediate reaction product; wherein:
        $M^1$ is a metal selected from the group consisting of Ti, Zr, Hf, Al or Si;
        $M^2$ is a metal being Si;
        v is the valency of $M^1$ or $M^2$;
        w is smaller than v;
        $R^2$ and $R^3$ are each a linear, branched or cyclic hydrocarbyl group independently selected from the group consisting of alkyl, alkenyl, aryl, aralkyl, alkoxycarbonyl, alkylaryl groups, and one or more combinations thereof; wherein said hydrocarbyl group is substituted or unsubstituted, and optionally contains one or more heteroatoms;
    iii) contacting the first or second intermediate reaction product obtained in step ib) or ii) respectively, with a halogen-containing titanium compound and either an activator or an internal electron donor to obtain a third intermediate reaction product;
    iv) optionally modifying the third intermediate reaction product obtained in step iii) with a modifier having the formula $MX_3$, wherein M is a metal selected from the Group 13 metals and transition metals of the IUPAC periodic table of elements, and wherein X is a halide, to yield a modified intermediate reaction product; and
    v) contacting said third intermediate reaction product obtained in step iii) or said modified intermediate reaction product obtained in step iv) with a halogen-containing titanium compound and in the case that in step iii) an activator was used an internal donor to obtain the procatalyst.

2. The process according to claim 1, wherein the activator added during step iii) is selected from the group consisting of alkyl benzoate, benzamide, and monoester.

3. The process according to claim 1, wherein the alkyl magnesium compound used in step ia) is dibutylmagnesium.

4. The process according to claim 1, wherein the Grignard reagent used in step ia) is butyl magnesium chloride.

5. The process according to claim 1, wherein the Grignard reagent used in step ia), and the halogen-containing titanium compound used in step iii) and step v) are used in such amounts that the resulting procatalyst comprises in wt. % based on the total weight of the procatalyst:magnesium: from 15 to 24; titanium: from 1 to 4.

6. The process according to claim 1, wherein step ii) is carried out using a combination of an alcohol and a tetra alkoxy titanium compound as the activating compounds.

7. The process according to claim 1, wherein the ratio between the alkyl magnesium and Grignard reagent is between 1:1 and 1:4.

8. The process according to claim 1, wherein a ratio of an amount of said tetrahalogensilane compound to the combined amount of magnesium of the Grignard reagent and the compound $MgR^{4'}{}_2$ is 0.2 to 5.

9. A procatalyst obtained by the process according to claim 1, said procatalyst comprising a titanium catalyst supported on a solid magnesium-containing support characterized in that the procatalyst comprises in wt. % based on the total weight of the procatalyst:magnesium: from 15 to 24; and titanium: from 1 to 4.

10. The procatalyst according to claim 9, wherein the procatalyst comprises in wt. % based on the total weight of the procatalyst:magnesium: from 19.0 to 19.5; and/or titanium: from 1.5 to 3.5.

11. A catalyst system for olefin polymerization comprising the procatalyst according to claim 9, a co-catalyst, and optionally an external electron donor.

12. The catalyst system according to claim 11, wherein the co-catalyst is an organometallic compound containing a metal from group 1, 2, 12 or 13 of the Periodic System of the Elements.

13. A process of preparing a polyolefin, the process comprising contacting at least one olefin with a polymerization catalyst system according to claim 11.

14. The process according to claim 1, wherein
    the activator added during step iii) is selected from the group consisting of alkyl benzoate, benzamide, and monoester;
    the alkyl magnesium compound used in step ia) is dibutylmagnesium;
    the Grignard reagent used in step ia) is butyl magnesium chloride;
    the Grignard reagent used in step ia), and the halogen-containing titanium compound used in step iii) and step v) are used in such amounts that the resulting procatalyst comprises in wt. % based on the total weight of the procatalyst:magnesium: from 15 to 24; titanium: from 1 to 4;

step ii) is carried out using a combination of an alcohol and a tetra alkoxy titanium compound as the activating compounds;

the ratio between the alkyl magnesium compound and Grignard reagent is between 1:1 and 1:4;

a ratio of an amount of said tetrahalogensilane compound to the combined amount of magnesium of the Grignard reagent and the compound $MgR^{4'}_2$ is 0.2 to 5.

15. The process according to claim 14, wherein $X^4$ and $X^1$ have from 1 to 20 carbon atoms;

$X^4$, $X^1$, and $X^{4'}$ are each chloride;

$R^2$ and $R^3$ each have from 1 to 20 carbon atoms;

step v) is carried out at least two times;

the activator is ethyl benzoate;

the Grignard reagent used in step ia), and the halogen-containing titanium compound used in step iii) and step v) are used in such amounts that the resulting procatalyst comprises in wt. % based on the total weight of the procatalyst:magnesium: from 18.0 to 19.5; titanium: from 1.5 to 3.5;

step ii) is carried out using an combination of ethyl alcohol and tetraethoxy titanium as the activating compounds; and said tetrahalogensilane compound is present in respect of the amount of magnesium of the Grignard reagent and the compound $MgR^{4'}_2$ in a ratio of 0.5 to 1.

16. A catalyst system for polymerization of ethylene or a mixture of ethylene and propylene, the method comprising:

a procatalyst obtained by the method of claim 14, said procatalyst comprising a titanium catalyst supported on a solid magnesium-containing support characterized in that the procatalyst comprises in wt. % based on the total weight of the procatalyst:magnesium: from 15 to 24; and titanium: from 1 to 4;

a co-catalyst, wherein the co-catalyst is an organometallic compound containing a metal from group 1, 2, 12 or 13 of the Periodic System of the Elements, and optionally an external electron donor.

17. A process of preparing a polyolefin, the process comprising contacting of ethylene or a mixture of ethylene and propylene with a polymerization catalyst system according to claim 16.

* * * * *